(12) United States Patent
Ginggen et al.

(10) Patent No.: US 7,437,644 B2
(45) Date of Patent: Oct. 14, 2008

(54) AUTOMATIC SELF-TESTING OF AN INTERNAL DEVICE IN A CLOSED SYSTEM

(75) Inventors: Alec Ginggen, Neuchâtel (CH); Rocco Crivelli, Bellinzona (CH)

(73) Assignee: Codman Neuro Sciences Sárl, Le Locle (CH)

( * ) Notice: Subject to any disclaimer, the term of this patent is extended or adjusted under 35 U.S.C. 154(b) by 771 days.

(21) Appl. No.: 10/978,247

(22) Filed: Oct. 29, 2004

(65) Prior Publication Data
US 2006/0107148 A1 May 18, 2006

(51) Int. Cl.
*G01R 31/28* (2006.01)
(52) U.S. Cl. .......................... 714/734; 714/25; 714/30; 714/47; 714/703; 714/733; 714/742; 714/745; 600/300; 604/891.1; 607/32; 607/33
(58) Field of Classification Search .................. None
See application file for complete search history.

(56) References Cited

U.S. PATENT DOCUMENTS

| 4,041,954 A | 8/1977 | Ohara |
|---|---|---|
| 4,281,664 A | 8/1981 | Duggan |
| 4,979,506 A | 12/1990 | Silvian |
| 5,899,926 A | 5/1999 | Ochs et al. |
| 6,021,352 A | 2/2000 | Christopherson et al. |
| 6,048,328 A | 4/2000 | Haller et al. |
| 6,317,633 B1 | 11/2001 | Jorgenson et al. |
| 6,329,822 B1 | 12/2001 | Powers |
| 6,387,048 B1 | 5/2002 | Schulman et al. |
| 6,622,043 B1 | 9/2003 | Kraus et al. |
| 6,648,821 B2 | 11/2003 | Lebel et al. |
| 6,721,600 B2 | 4/2004 | Jorgenson et al. |
| 6,740,075 B2 | 5/2004 | Lebel et al. |
| 2002/0087113 A1 | 7/2002 | Hartlaub |
| 2002/0198513 A1 | 12/2002 | Lebel et al. |
| 2006/0069412 A1 | 3/2006 | Ginggen et al. |

*Primary Examiner*—John P Trimmings
(74) *Attorney, Agent, or Firm*—Cheryl F. Cohen, LLC

(57) ABSTRACT

A closed system such as a TET system in which self-testing of all components of the implantable medical device whose malfunction could negatively impact on the proper operation of the closed system is automatically and periodically performed without triggering from an external device. In addition, a closed system including automatic, periodic self-testing of the implantable medical device in which, whenever practical, testing of the components is synchronized with telemetric communication of the external device whereby an external RF field generated by the external device is used to supply necessary power to perform self-testing.

16 Claims, 2 Drawing Sheets

AUTOMATIC SELF-TESTING OF AN INTERNAL DEVICE IN A CLOSED SYSTEM

BACKGROUND OF THE INVENTION

1. Field of the Invention

The present invention is directed to self-testing of an internal device in a closed system and, in particular, to an implantable medical device in a transcutaneous energy transfer (TET) system that performs automatic, periodic self-testing to verify its proper operation while minimizing power consumption.

2. Description of Related Art

In a variety of scientific, industrial, and medically related applications, it may be desirable to transfer energy or power (energy per unit time) across some type of boundary. For example, one or more devices that require power (e.g., electrical, mechanical, optical, and acoustic devices) may be located within the confines of a closed system, or "body," in which it may be difficult and/or undesirable to also include a substantial and/or long term source of power. The closed system or body may be delimited by various types of physical boundaries, and the system internal to the boundary may be living or inanimate, may perform a variety of functions, and may have a variety of operational and physical requirements and/or constraints. In some cases, such requirements and constraints may make the implementation of a substantial and/or long term "internal" power source for internally located devices problematic.

In some closed systems, repeated entry into the system may be undesirable for a variety of reasons. In other closed systems, significant internal power requirements and a limited internal space may prohibit the implementation of a suitably sized internal power source. In yet other systems, contamination and/or security issues may pose particular challenges in implementing an internal power source. For any combination of the foregoing and other reasons, a power source external to the system and some feasible means of transferring power from the external source to one or more internal devices may be preferable in some applications.

One common example of a closed system is the human body. In some medically related and scientific applications, a variety of prosthetic and other medical-devices that require power may be surgically implanted within various portions of the body. Some examples of such devices include, but are not limited to, drug infusion pumps, pacemakers, defribllators, cochlear implants, sensors and stimulators. With respect to the human body, issues such as repeated reentry or surgery, internal space limitations, and contamination (e.g., infection) are factors to consider when selecting a suitable internal power source for some of these implantable medical devices.

Accordingly, in some medical implant applications, "transcutaneous energy transfer" (TET) devices are employed to transfer energy from outside the body to inside the body, to provide power to one or more implanted prostheses or devices from an external power source. One example of a conventional TET device is a transformer that includes a primary winding (or coil) external to the body and a secondary winding internal to the body. Both the primary and secondary windings generally are placed proximate to respective outer and inner layers of a patient's skin; hence, the term "transcutaneous" commonly refers to energy transfer "through the skin."

Like any electronic device implantable medical devices are subject to possible malfunction or may cease functioning altogether. Because some of the medical devices provide life threatening functionality, it is imperative to test to ensure proper operation. Heretofore testing of implantable electronic devices was often initiated by an individual such as a physician, technician, nurse or patient upon engaging a button or key on an external control device in communication with the implantable medical device. Desirably such testing would be triggered periodically, for example, once every 24 hours, to verify proper operation. This disadvantageously would require someone to remember to manually activate or initiate the testing procedure.

In order to eliminate all possibility of human error in forgetting to initiate testing, means for automatically activating a self-testing sequence have been developed. For instance, U.S. Pat. No. 6,387,048 discloses an implantable sensor which includes electronic circuitry for automatically performing on a periodic basis, e.g., once every hour or once every day, specified integrity tests in order to verify proper operation of the sensor. A plurality of sensors are implanted in a patient in the same general area. Each sensor operates independently of the others. If all the sensors are functioning properly, then the output data obtained from each sensor should be approximately the same. The output data sensed by each sensor may thus be used as a cross-check against the output data sensed by the other sensors. However, the teaching of this patent is limited to checking of only high level output data detected by the sensor, and fails to check the low level operation of the components themselves. This is problematic in that the invention fails to identify the specific component that is subject to malfunction.

Other patents such as U.S. Pat. No. 6,740,075 disclose a TET system with self-testing functionality initiated at the external communication device. Software associated with the communication device, in turn, generates an Initiate Self-Test telemetry message that is transmitted via telemetry to the implantable device so that it may be tested as well. Another aspect of the testing functionality taught by the patented invention involves self-testing of the battery voltage of the implantable medical device. The communication device telemetry system sends messages to or receives messages from the medical device telemetry system, wherein the communication device is capable of performing a test of battery voltage with a load on the battery. Additional variations are described in which at least one of the following will occur, (1) the battery voltage is also automatically and periodically checked with the battery under a minimal load, (2) at least one selected electrical component is forced on to produce the load for testing, or (3) the test is made to occur at least in part when at least one selected electrical component is powered on in the performance of its normal operation, wherein the electrical component provides a load for the testing. Accordingly, this patented invention discloses self-testing of the implantable medical device (e.g., battery voltage) in response to a triggering signal generated by the external communication device.

Accordingly, the TET system taught by U.S. Pat. No. 6,740,075 requires a triggering signal from the external device to initiate automatic, periodic self-testing functionality of the internal battery power. In addition, except for battery power, all remaining components of the implantable medical device, in particular all other components whose malfunction could negatively impact the health of the patient, fail to be tested. Furthermore, such testing of the battery voltage is conducted periodically based solely on the expiration of predetermined periodic time periods or each time the device is powered on and thus is inefficient from an energy consumption perspective. As discussed above, in a closed system such as that employing an implantable medical device and external control unit each has its own coil for receiving/transmitting radio frequency signals therebetween. In addition, each of the implantable medical device and external control unit has its own associated power source, e.g., a battery, for powering its associated circuitry and its associated components. The battery, regardless of whether primary/non-rechargeable or secondary/rechargeable, has a limited lifespan and a predetermined amount of energy or power before having to be replaced or recharged. Testing to verify that the implantable medical device is working properly consumes energy from the limited internal battery power source thereby reducing its overall lifespan. Accordingly, heretofore the advantages of automatic, periodic self-testing of an implantable medical device to verify proper operation had to be weighed against the disadvantageous consumption of battery power and thus reduction in lifespan.

It is therefore desirable to develop an improved TET device that solves the aforementioned problems by conducting automatic, periodic self-testing functionality of multiple components, preferably all components whose malfunction could negatively impact the health of the patient, of the implantable medical device without triggering from an external device. Furthermore, it would be beneficial to design an improved TET device that automatically initiates periodic self-testing of the implantable device, of any number of one or more components, while minimizing or optimizing the amount of energy consumed or drawn from its internal power source.

SUMMARY OF THE INVENTION

An object of the present invention is to design a TET system that performs automatic, periodic self-testing functionality of multiple components of the implantable medical device, preferably all components whose malfunction could negatively impact the health of the patient, without triggering from an external device. Simultaneous self-testing of multiple components, preferably all components whose malfunction could negatively impact the health of the patient, on an automatic, periodic basis minimizes energy consumption.

Another object of the invention is to develop a TET system wherein the implantable device triggers automatic, periodic self-testing, of one or more components to verify proper operation while minimizing power consumption of the internal power source.

These and other objects of the invention are realized in the present inventive closed system that includes an internal device disposed interior of a boundary and having an internal power source. An external device is separated from the internal device by and disposed exterior to the boundary. The external device is in telemetric communication with the internal device and generates an external RF energy source during telemetric communication with the internal device. A system clock counts down a predetermined period of time. The closed system further includes self-testing circuitry for verifying proper operation of at least one component of the internal device. The self-testing circuitry is automatically triggered upon the expiration of the predetermined period of time on the system clock. RF circuitry detects the presence and level of the external RF field received by the internal device. A microprocessor initiates the self-testing circuitry and resets the system clock in the presence of a detected external RF field when the time remaining on the system clock is less than a predetermined reset time period. In a preferred embodiment, the closed system is a transcutaneous energy transfer system and the internal device is an implantable medical device.

The invention also is directed to a method for operating the closed system described above. Specifically, a predetermined period of time is counted down using a system clock. Upon the expiration of the predetermined period of time on the system clock, self-testing circuitry is automatically triggered for verifying proper operation of at least one component of the internal device. The presence and level of an external RF field received by the internal device is detected. In the presence of a detected external RF field when the time remaining on the system clock is less than a predetermined reset time period, the self-testing circuitry is initiated and the system clock is reset.

In yet another embodiment, the present invention relates to a closed system including an internal device disposed interior of a boundary, an external device separated from the internal device by and disposed exterior to the boundary and a system clock for counting down a predetermined period of time. The closed system further includes self-testing circuitry for verifying proper operation of all components of the internal device whose malfunction could negatively impact on proper operation of the closed system, the self-testing circuitry is automatically triggered upon the expiration of the predetermined period of time on the system clock without a triggering signal from the external device. In a preferred embodiment the closed system is a transcutaneous energy transfer system and the self-testing circuitry verifies proper operation of all components of an implantable medical device whose malfunction could negatively impact on the health of a patient in whom the medical device is implantable. The invention is also directed to a method of operating this closed system. Such method includes the steps of: (i) counting down a predetermined period of time using a system clock; and (ii) automatically initiating upon the expiration of the predetermined period of time on the system clock, without a triggering signal from the external device, self-testing circuitry for verifying proper operation of all components of the internal device whose malfunction could negatively impact on proper operation of the closed system.

BRIEF DESCRIPTION OF THE DRAWING

The foregoing and other features of the present invention will be more readily apparent from the following detailed description and drawings of illustrative embodiments of the invention wherein like reference numbers refer to similar elements throughout the several views and in which.

DETAILED DESCRIPTION OF THE INVENTION

The present invention is directed to a closed system and method for self-testing of a first internal electronic device in telemetric communication with a second external electronic device, wherein each electronic device has its own power source. If any error in operation of the internal electronic device is detected, then a buzzer, vibrator alarm and/or some other indicator is activated to alert the user. By way of example, the TET system shown and described is an implantable medical device, e.g., a drug infusion pump, in telemetric communication with an external device, e.g., an external control unit, personal computer, mobile or cellular telephone, or Personal Digital Assistant (PDA). It is to be understood, however, that the present invention may be used for other devices and is not limited in application to the medical field.

Figure 1:
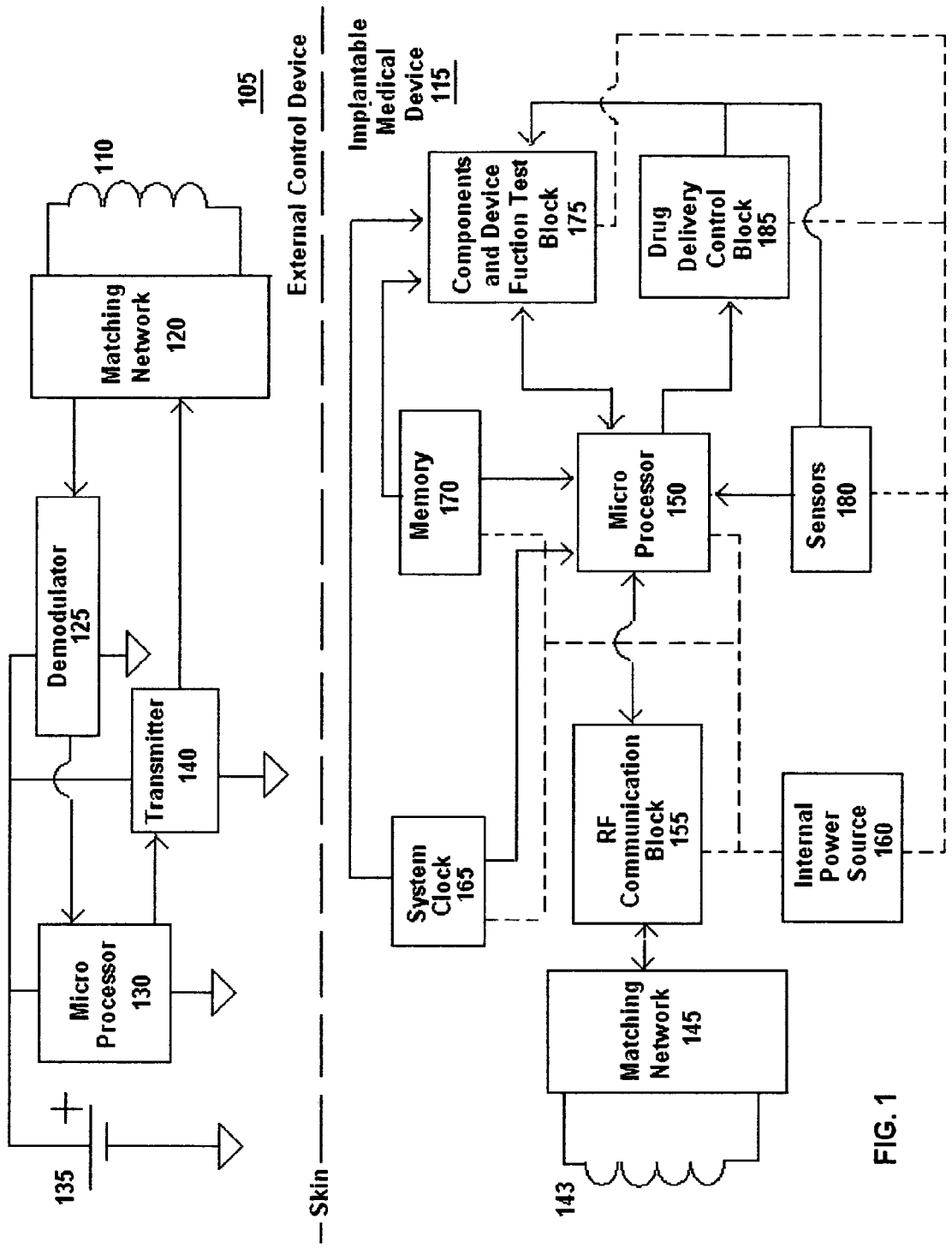
FIG. 1 is an exemplary schematic diagram of a transcutaneous energy transfer system between an external control unit and an automatic self-testing implantable medical device.

FIG. 1 shows a schematic diagram of a TET system including an external device 105 (e.g., an external control unit) in telemetric communication with an implantable medical device 115 (e.g., a drug infusion pump, stimulator, sensor). External device 105 includes a primary coil 110 electrically connected to a tuned matching network 120 that transmits and receives RF data. A demodulator 125 for extracting data signals from the received carrier signal is, in turn, electrically connected to the matching network 120. The output of the demodulator 125 is connected to a microprocessor 130. A transmitter 140 is electrically connected between the microprocessor 130 and matching network 120. All components and circuitry associated with the external device 105 are powered by a power source 135, e.g., a battery. In a preferred embodiment, the power source 135 for powering the external device 105 and its associated circuitry and components is a secondary/rechargeable battery, most preferably a smart rechargeable battery.

Implantable medical device 115 has an associated secondary coil 143, a matching network 145, RF communication block 155, and microprocessor 150. RF communication block 155 transmits/receives and respectively modulates/demodulates the RF data signals. In addition, RF communication block 155 detects the presence of an RF field generated by the external device 105 during communication with the implant and, in turn, triggers powering of the implant communication components. Microprocessor 150 is connected to a system clock 165, a memory device 170, and testing circuitry 175 for verifying the operation of one or more components of the implantable medical device 115. Since the example shown in FIG. 1 is for an implantable drug infusion pump, the implantable medical device further includes: (i) sensors 180 for detecting information related to the physical state or condition of the patient and/or the implant device; and (ii) drug delivery control circuitry 185 for varying the flow of dispensing medication to the patient based on the sensed state or condition of the patient. Internal power source 160 is used to power the implantable medical device 115 and all components and circuitry associated therewith (as denoted by the dashed lines in FIG. 1). In the case in which the implantable medical device 115 (e.g., a drug infusion pump) is designed to provide power to the components and circuitry associated therewith at all times, the power source 160 is preferably a primary/non-rechargeable battery.

System clock 165 counts down a predetermined period of time the expiration of which activates, initiates or triggers testing circuitry 175 for performing steps to ensure or verify proper operation of any desired functionality and components of the implantable medical device 115. Preferably, the predetermined period of time is set for once every 24 hours, i.e., once a day. Nevertheless, this time period may be modified, as desired, for example, to test multiple times a day, every other day, once a week, once a month, annually, or any other desired time frame.

Testing circuitry 175 verifies the proper operation of the implantable medical device 115. Self-testing data is stored in memory 170, preferably a non-volatile memory device. By way of example, the testing circuitry 175 performs diagnostics to confirm the proper operation of any one or more of the following components: (i) memory check (e.g., read/write operation of RAM) (ii) flash check (e.g., CRC for flash code memory tested; CRC for flash information memory tested); (iii) non-volatile programmable memory read check and CRC check of the memory content; (iv) battery voltage level check; and (v) crystal frequency check. Additional high level testing may be conducted such as temperature sensor check, drug level check and drug flow check.

The tests conducted, may be varied, as desired, depending upon the type of device and its associated components employed in the TET system. Preferably, all components whose malfunction could have a negative impact on the health of the patient, are automatically and periodically tested triggered by the countdown to zero of the predetermined period of time. Such components may include high level (i.e., output level) testing such as the dispensing of the proper dosage of medication or level of energy stimulus; and/or low level (i.e., component level) testing such as the proper operation of a memory device. It is efficient to simultaneously test multiple components at the same time as part of the self-testing process to optimize energy consumption. By way of example, many of the components in the exemplary drug infusion pump, in a preferred embodiment, are in a sleep mode (i.e., powered off) prior to triggering of the automatic self-testing sequencing. When self-testing is initiated, the components previously in sleep mode are powered on and each micro-controller starts the self-test process. In the case in which multiple microprocessors are employed, each microprocessor is able to perform testing on different components in parallel thereby reducing energy consumption. Moreover, any single processor may perform multiple tests simultaneously or in concert, thereby further reducing power consumption. For instance, a single processor may be programmed to measure the frequency that is generated by the signal conditioning circuit connected to the drug level sensor and also verify memory CRC. To achieve this end, a counter may be triggered by the microprocessor to measure the frequency of the drug level sensor. While the counter is running, the same microprocessor may initiate a calculation of the CRC. Therefore, simultaneous, automatic, periodic self-testing of multiple components saves energy by combining the self-testing processes.

In operation self-testing circuitry 175 is automatically triggered by the implantable device each time the system clock 165 counts down from the predetermined time interval, preferably 24 hours, to zero. In addition to automatic, periodic self-testing, manual or on demand testing may also be triggered or initiated by the user, physician, technician, or nurse at any time in response to a request signal generated by the external device 105. Such manual or on demand testing requests by the external device 105 preferably does not interrupt or reset automatic, periodic self-testing of the implantable device.

The implantable medical device 115 requires energy to carry out testing. Heretofore, the energy necessary to power an implantable medical device including that necessary for testing was drawn from the internal power source 160 associated with the implantable medical device 115 itself. It is desirable while testing to conserve or minimize the power drawn from the internal power source 160 associated with the implantable device by switching to an alternative external power source. Referring to FIG. 1, the RF communication block 155 in the implantable medical device 115 further includes an RF/DC transformer for converting the incoming RF signal generated by the external device 105 to a DC voltage. Power switching circuitry is also included in the RF communication block 155 for commuting power from the external RF field generated by the external device 105 during communication with the implant rather than from the limited internal power source 160. Exemplary power switching circuitry for commuting from the limited internal power source 160 to energy extracted from external RF emissions produced during communication by the external device to the implant in order to power the implantable medical device 115 is described in U.S. patent application Ser. No. 10/955,678, entitled "Dual Power Supply Switching Circuitry for Use in a Closed System", filed on Sep. 30, 2004, and herein incorporated by reference in its entirety.

It would be desirable to synchronize or coordinate self-testing of the implantable medical device components during communication of the external device 105 with the implantable medical device 115 so that the external RF field emissions produced by the external device may be used to supplement or replace energy otherwise drawn from the internal power source 160. Accordingly, the energy necessary to perform the self-testing operations of the implantable medical device 115 may be obtained, whenever practical, from the external RF emissions rather than from the limited stored power of the internal power source 160.

Figure 2:
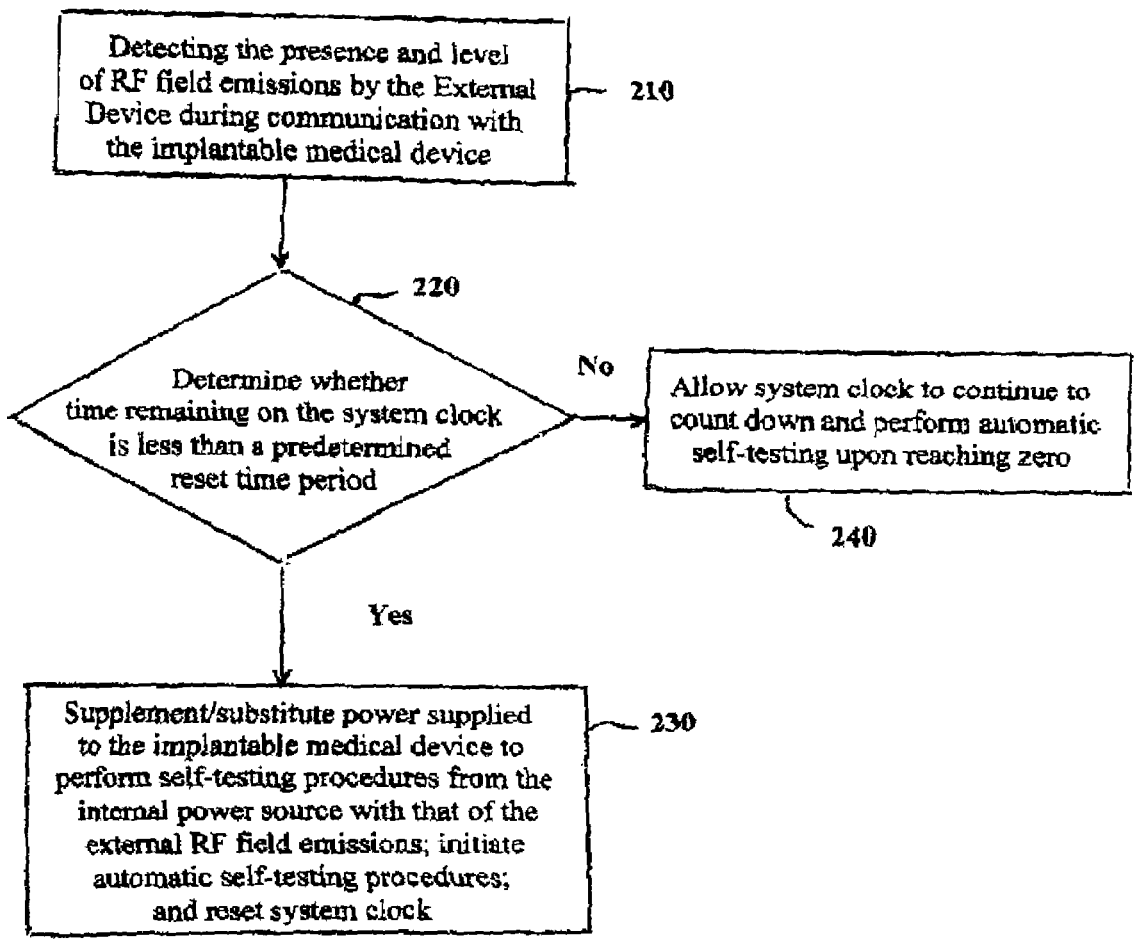
FIG. 2 is an exemplary flow chart of the operation of the automatic self-testing of the implantable medical device of FIG. 1.

FIG. 2 is an exemplary flow chart of the operation of the automatic self-testing system in accordance with a second embodiment of the present invention. System clock 165 associated with the implantable medical device 115 continuously counts down a predetermined period of time, e.g., every 24 hours, and automatically triggers the testing circuitry 175 upon reaching zero. RF communication block 155 detects the presence and level of an RF field emitted by the external device 105 during communication with the implantable medical device 115, as found in step 210. It is inefficient to trigger self-testing and resetting of the system clock 165 based solely on whether an external RF field is detected because under certain circumstances communication may occur within a relatively short period of time of each other and testing of the implant so frequently is not necessary. To overcome such inefficiency, upon detecting the presence of an external RF field, microprocessor 150 determines whether the time remaining on the system clock 165 (i.e., the time remaining on the clock before initiating automatic self-testing) is sufficiently small to warrant resetting the clock and initiating automatic self-testing powered entirely, or at least in part, by the external RF power source. This determination is made in step 220 by the microprocessor 150 by comparing the time remaining on the system clock 165 with that of a predetermined reset time period. In general, if the time remaining on the system clock 165 when an external RF field is detected is greater than or equal to the predetermined reset time period then self-testing has recently been performed and testing again so soon in time is not necessary. Accordingly, the system clock is allowed to count down uninterrupted and testing is automatically triggered upon reaching zero, as shown in step 240. On the other hand, if an external RF field is detected when the amount of time remaining on the system clock is less than the predetermined reset time period then self-testing having not been recently performed is forced to occur. Specifically, in step 230, under such circumstances, testing circuitry 175 is initiated and the system clock 165 is reset. Power required for testing of the implantable medical device components is either supplemented or substituted for that supplied by the internal power source 160 depending on the level of detected external RF field emissions generated by the external device 105 during communication with the implant 115.

In an illustrative example, system clock 165 counts down the predetermined period of time (e.g., 24 hours) and automatically initiates testing upon reaching zero, e.g., at 11:59 pm every day. The predetermined reset time period is set to 2 hours. If detection of an external RF field occurs when less than two hours remain on the system clock 165, then microprocessor 150 sends a reset signal to system clock 165, the clock is reset to count down the predetermined period of time, and testing circuitry 175 is triggered or initiated. Energy necessary to perform the self-testing procedures otherwise drawn from the internal power source 160 is supplemented or replaced by that supplied by the external RF field depending on the level of power generated by the external device. Continuing with the illustrative example, on the first day testing is performed automatically at 11:59 pm (i.e., at the expiration of the 24 hour count down by the system clock 165). Once again, on day two testing of the implantable medical device is automatically triggered at 11:59 pm. At 12:00 pm on day three, RF communication block 155 detects the presence of an external RF field with 12 hours remaining on the system clock 165. Since the detection of the RF field occurs when more than the 2 hour predetermined reset time period remains on the system clock 165, the clock continues to run and testing circuitry 175 is automatically initiated at the end of the count down of the remaining 12 hours when the system clock reaches zero. On day four an external RF field is detected by the RF communication block 155 at 11:00 pm, with less than 2 hours remaining on the system clock 165. In this scenario, the system clock 165 is reset upon receiving a reset signal from microprocessor 150 and testing circuitry 175 is automatically triggered at a new time of 11:00 pm. Assuming that no external RF power source is detected on day five, then the system clock will count down the 24 hour predetermined time period and automatically trigger self-testing at 11:00 pm on day five.

If automatic self-testing is triggered in the presence of the external RF field, i.e., during communication of the external device with the implant, then the external RF field either supplements or replaces energy that would otherwise be drawn from the internal power source 160 to perform self-testing. Specifically, if the power supplied by external RF energy exceeds that required to perform self-testing of the implant, then the internal power source 160 is cut off and all power is extracted from the external RF energy source. However, if the power produced by the external RF energy source is less than that required to perform self-testing, then the amount of energy drawn from the internal power source 160 is reduced by the amount of power captured from the external RF energy source. Alternatively, the system can be designed so that there is no sharing of power between the internal power source and external RF field. In this alternative embodiment, powering of the testing electronics is supplied either exclusively by the internal power source 160 or by the external RF field. In particular, if there is no detection of the presence of an external RF field or the power emitted by the external RF field is not sufficient for that required to perform self-testing then power is continues to be drawn from the internal power source 160. Otherwise, the power used to perform or conduct self-testing of the components of the implantable medical device 115 is drawn from the external RF energy source via the power switching circuitry 195 when it exceeds that required to perform self-testing.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A closed system comprising:
   an internal device disposed interior of a boundary;
   an internal power source for powering the internal device;
   an external device separated from the internal device by and disposed exterior to the boundary, the external device being in telemetric communication with the internal device and generating an external RF energy source during telemetric communication with the internal device;
   a system clock for counting down a predetermined period of time;
   self-testing circuitry for verifying proper operation of at least one component of the internal device, the self-testing circuitry being automatically triggered upon the expiration of the predetermined period of time on the system clock;
   RF circuitry for detecting the presence and level of an external RF field received by the internal device; and
   a microprocessor for initiating the self-testing circuitry and resetting the system clock in the presence of a detected external RF field when the time remaining on the system clock is less than a predetermined reset time period.

2. The closed system in accordance with claim 1, further comprising power switching circuitry connected to the microprocessor to cut off power from the internal power source and draw power exclusively from the external RF field when the power generated by the external RF field exceeds that required for performing self-testing of the at least one component of the internal device.

3. The closed system in accordance with claim 1, wherein the microprocessor supplements power extracted from the internal power source by power drawn from the external RF field when the power generated by the external RF field is less than that required for performing self-testing of the at least one component of the internal device.

4. The closed system in accordance with claim 1, wherein the predetermined period of time is approximately 24 hours and the predetermined reset time period is approximately 2 hours.

5. The closed system in accordance with claim 1, wherein the self-testing circuitry performs low level diagnostics that includes at least one of: (i) memory check; (ii) flash memory check; (iii) non-volatile programmable memory read check and CRC check of memory content; (iv) battery voltage level check; and (v) crystal frequency check.

6. The closed system in accordance with claim 1, wherein the self-testing circuitry performs high level diagnostics of the internal device.

7. The closed system in accordance with claim 6, wherein the high level diagnostics includes at least one of: (i) temperature sensor check, (ii) drug level check, and (iii) drug flow check.

8. The closed system in accordance with claim 1, wherein the closed system is a transcutaneous energy transfer system and the internal device is an implantable medical device.

9. A method for automatic self-testing in a closed system an interval device having an internal power source separated by a boundary from an external device disposed exterior to the boundary, the external device being in telemetric communication with the internal device and generating an external RF energy source during telemetric communication with the internal device, the method comprising the steps of:
   counting down a predetermined period of time using a system clock;
   automatically triggering upon the expiration of the predetermined period of time on the system clock self-testing circuitry for verifying proper operation of at least one component of the internal device;
   detecting the presence and level of an external RF field received by the internal device; and
   in the presence of a detected external RF field when the time remaining on the system clock is less than a predetermined reset time period, initiating the self-testing circuitry and resetting the system clock.

10. The method in accordance with claim 9, wherein the initiating step further comprises the step of cutting off power from the internal power source and drawing power exclusively from the external RF field, when the power generated by the external RF field exceeds that required for performing self-testing of the at least one component of the internal device.

11. The method in accordance with claim 9, wherein the initiating step further comprises the step of supplementing power extracted from the internal power source by power drawn from the external RF field, when the power generated by the external RF field is less than that required for performing self-testing of the at least one component of the internal device.

12. The method in accordance with claim 9, wherein the predetermined period of time is approximately 24 hours and the predetermined reset time period is approximately 2 hours.

13. The method in accordance with claim 9, wherein the triggering step comprises the step of performing low level diagnostics that includes at least one of: (i) memory check; (ii) flash memory check; (iii) non-volatile programmable memory read check and CRC check of memory content; (iv) battery voltage level check; and (v) crystal frequency check.

14. The method in accordance with claim 9, wherein the triggering step comprises the step of performing high level diagnostics of the internal device.

15. The method in accordance with claim 14, wherein the high level diagnostics includes at least one of: (i) temperature sensor check, (ii) drug level check, and (iii) drug flow check.

16. The method in accordance with claim 9, wherein the closed system is a transcutaneous energy transfer system and the internal device is an implantable medical device.

* * * * *